US008137283B2

(12) United States Patent
Syeda-Mahmood et al.

(10) Patent No.: US 8,137,283 B2
(45) Date of Patent: Mar. 20, 2012

(54) METHOD AND APPARATUS FOR RETRIEVAL OF SIMILAR HEART SOUNDS FROM A DATABASE

(75) Inventors: Tanveer Fathima Syeda-Mahmood, Cupertino, CA (US); Fei Wang, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 804 days.

(21) Appl. No.: 12/196,821

(22) Filed: Aug. 22, 2008

(65) Prior Publication Data
US 2010/0049072 A1 Feb. 25, 2010

(51) Int. Cl.
*A61B 5/02* (2006.01)
(52) U.S. Cl. ...................................... 600/528
(58) Field of Classification Search .............. 600/528; 607/9, 17, 18, 23, 24; 381/67
See application file for complete search history.

(56) References Cited

U.S. PATENT DOCUMENTS

| | | | |
|---|---|---|---|
| 5,010,889 A * | 4/1991 | Bredesen et al. ............ | 600/528 |
| 5,025,809 A | 6/1991 | Johnson et al. | |
| 5,218,969 A | 6/1993 | Bredesen et al. | |
| 5,273,049 A | 12/1993 | Steinhaus et al. | |
| 6,480,737 B1 | 11/2002 | Policker et al. | |
| 7,031,765 B2 | 4/2006 | Ritscher et al. | |
| 7,243,064 B2 | 7/2007 | Paris | |
| 2008/0004904 A1 | 1/2008 | Tran | |

OTHER PUBLICATIONS

Wang, et al. ("Finding Disease Similarity by Combining ECG with Heart Auscultation Sound" Computers in Cardiology; 2007; 24:261-264).*
Abdalla S.A. Mohamed, et al. ("Recognition of Heart Sounds and Murmurs for Cardiac Diagnosis" Pattern Recognitionm, 1998, pp. 1009-1011 vol. 2).*
Hu et al., "A Single-lead ECG Enhancement Algorithm Using a Regularized Data-Driven Filter," IEEE Transactions on Biomedical Engineering, V53, N2, Feb. 2006, pp. 347-351.
Tuzcu et al., "Dynamic Time Warping as a Novel Tool in Pattern Recognition of ECG Changes in Heart Rhythm Disturbances," IEEE Int'l Conf. on Systems, Man & Cybernetics, Oct. 2005, V1, pp. 182-186.

* cited by examiner

*Primary Examiner* — Niketa Patel
*Assistant Examiner* — Hiba El-Kaissi
(74) *Attorney, Agent, or Firm* — IP Authority, LLC; Ramraj Soundararajan

(57) ABSTRACT

The present invention exploits a visual rendering of heart sounds and models the morphological variations of audio envelopes through a constrained non-rigid translation transform. Similar heart sounds are then retrieved by recovering the corresponding alignment transform using a variant of shape-based dynamic time warping.

17 Claims, 13 Drawing Sheets

METHOD AND APPARATUS FOR RETRIEVAL OF SIMILAR HEART SOUNDS FROM A DATABASE

BACKGROUND OF THE INVENTION

1. Field of Invention

The present invention relates generally to the field of audio pattern matching. More specifically, the present invention is related to matching heart sounds to previously diagnosed heart sounds assisting in physician decision.

2. Discussion of Related Art

Multimedia data is widely used in medical diagnosis through auditory and visual examination by physicians. In particular, heart auscultations and ECGs are two very important and commonly used diagnostic aids in cardiovascular disease diagnosis. While physicians routinely perform diagnosis by simple heart auscultation and visual examination of ECG waveform shapes, these two modalities reveal different diagnostic information about the heart. The heartbeat, for example, can reveal abnormal sounds caused by valvular disease, pericarditis, and dysrhythmia. On the other hand, the ECG unveils abnormal electrical activity during the contraction of the myocardium.

Single ECG analysis and ECG classification are well researched fields, and the popular techniques include neural network, machine learning methods, wavelet transforms and genetic algorithms. The rule-based methods rely on the accuracy of the P-Q-R-S-T segment detection. Errors in estimation of these feature values can cause major errors in disease-specific interpretation. The parametric modeling methods, on the other hand, are good at spotting major disease differences but can't take into account fine morphological variability due to heart rate (eg., ventricular vs. supra-ventricular tachycardia) and physiological differences. Related work in the time alignment of ECGs also exists.

Automatic analysis of heart sounds has been investigated for detecting heart abnormalities. The predominant approach in heart sound analysis is based on feature extraction and classification, as is conventional for audio analysis. These features can be roughly classified into two categories, the spatio-temporal features, such as the zero-crossing rate (ZCR), hidden Markov features etc., or frequency-domain features, such as Mel-frequency Cepstral Coefficients (MFCC).

U.S. Pat. Nos. 5,273,049; 7,031,765; and 6,480,737 describe matching electrocardiogram data to detect specific heart defects. These references do not match any sort of sound data. U.S. Pat. Nos. 5,218,969 and 5,025,809 process heart sound data to extract features (pitch/frequency, phase/sub-phase, etc.) from the heart sound and compare those extracted features to ranges of values which trigger rules for various diseases.

Whatever the precise merits, features, and advantages of the above cited references, none of them achieves or fulfills the purposes of the present invention.

SUMMARY OF THE INVENTION

In one embodiment, the present invention provides a computer-implemented method for detecting audio similarity of heart sounds comprising: recording a first heart sound, pre-processing the first heart sound, wherein the pre-processing comprises: selecting a time duration of a portion of the first heart sound to use as a second heart sound, constructing a line segment approximation of the second heart sound, defining an audio envelope around the second heart sound using the line segment approximation, isolating a plurality of fiducial points on the audio envelope, and matching the second heart sound to a plurality of similar heart sounds, wherein the matching comprises: identifying a non-rigid alignment transform based on a shape-based dynamic time warping to determine a correspondence between the fiducial points of the audio envelope and fiducial points from a database of heart sounds, defining a measure of shape similarity by determining a ratio of matched fiducial points to a total number of fiducial points, and ranking the matching based on the ratio.

In another embodiment, the present invention provides for a computer program product comprising: a computer usable medium having computer usable program code for detecting audio similarity of heart sounds, said computer program product including: computer usable program code for recording a first heart sound, computer usable program code for pre-processing the first heart sound, wherein the computer usable program code for pre-processing comprises: program code for selecting a time duration of a portion of the first heart sound to use as a second heart sound, computer usable program code for constructing a line segment approximation of the second heart sound, computer usable program code for defining an audio envelope around the second heart sound using the line segment approximation, computer usable program code for isolating a plurality of fiducial points on the audio envelope, and computer usable program code for matching the second heart sound to a plurality of similar heart sounds, wherein the computer usable program code matching comprises: program code for identifying a non-rigid alignment transform based on a shape-based dynamic time warping to determine a correspondence between the fiducial points of the audio envelope and fiducial points from a database of heart sounds, program code for defining a measure of shape similarity by determining a ratio of matched fiducial points to a total number of fiducial points, program code for ranking the matching based on the ratio.

DESCRIPTION OF THE PREFERRED EMBODIMENTS

Figure 1:
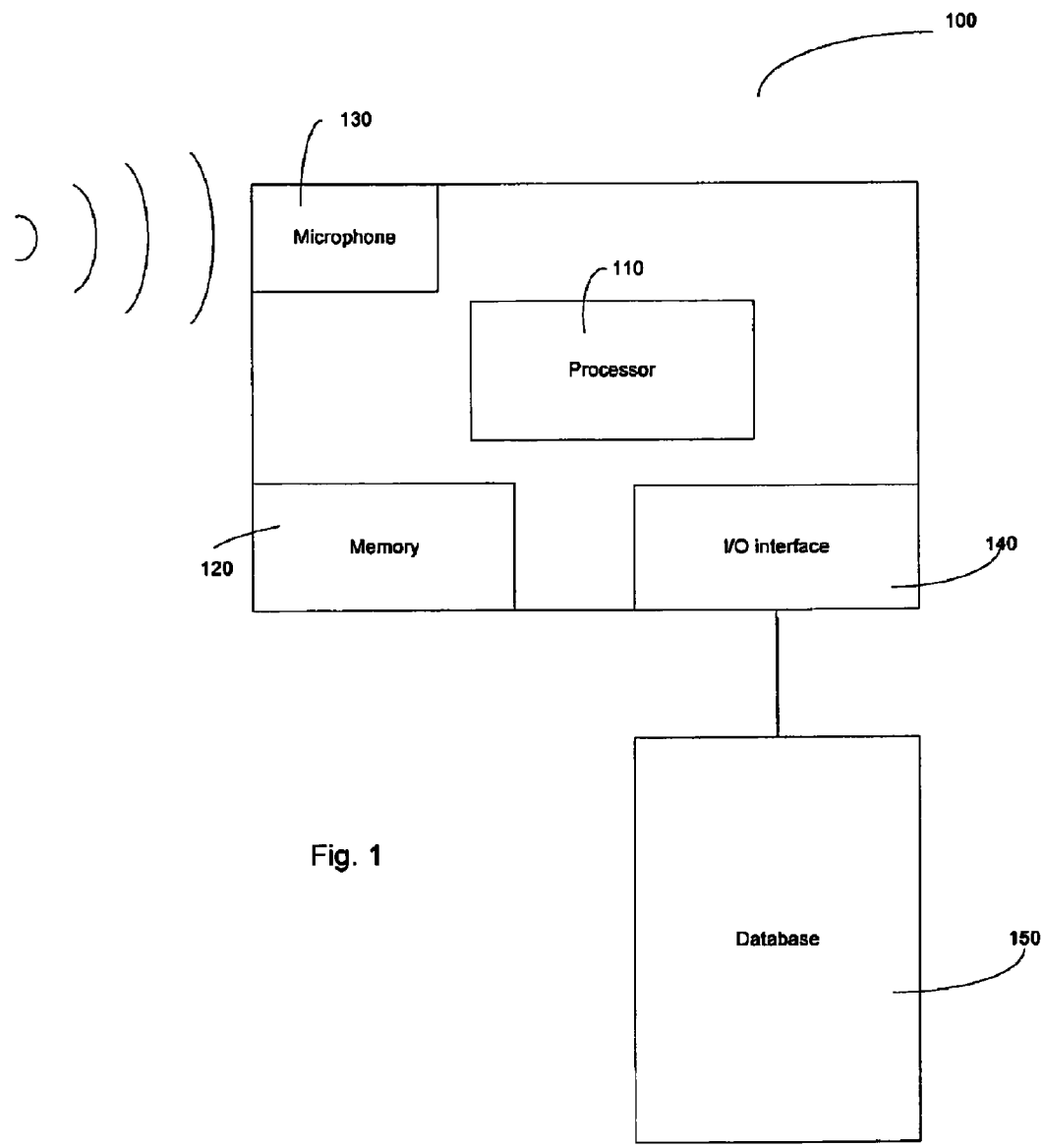
FIG. 1 illustrates a computer hardware system for implementing one embodiment of the present invention.

While this invention is illustrated and described in a preferred embodiment, the invention may be produced in many different configurations. There is depicted in the drawings, and will herein be described in detail, a preferred embodiment of the invention, with the understanding that the present disclosure is to be considered as an exemplification of the principles of the invention and the associated functional specifications for its construction and is not intended to limit the invention to the embodiment illustrated. Those skilled in the art will envision many other possible variations within the scope of the present invention.

The present invention records sounds for comparison with a database of potentially similar sounds. While the preferred embodiment comprises heart sounds compared with a database of heart sounds for disease and defect identification, the present invention may be used in other applications such as bird songs or human voices.

FIG. 1 shows a computer hardware system 100 used in implementing the method and program code of a preferred embodiment. Computer system 100 comprises a processor 110, memory 120, microphone 130, input/output interface 140, and database 150. Memory 120 stores sounds recorded by microphone 130. In one embodiment, the recorded sounds are heart sounds from a patient. Input/output interface 140 communicates with database 150, which stores a plurality of stored sounds. In one embodiment, the stored sounds comprise previously recorded heart sounds, which have been categorized according to diagnosis. After the similar heart sounds are identified from the database, their associated disease labels are used to form a distribution of related diseases for physician decision support.

Figure 2:
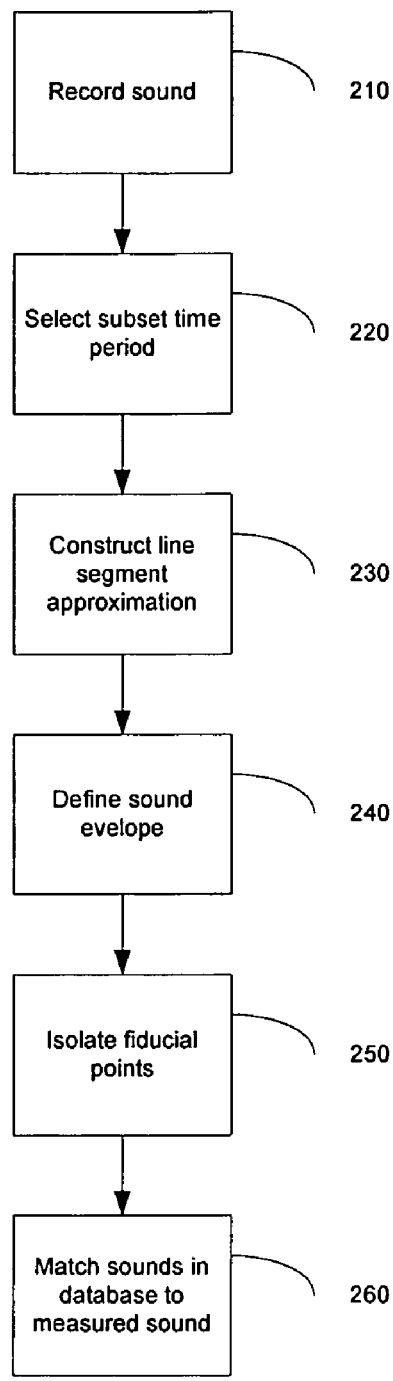
FIG. 2 illustrates a flowchart of the operation of an embodiment of the present invention.
Figure 3:
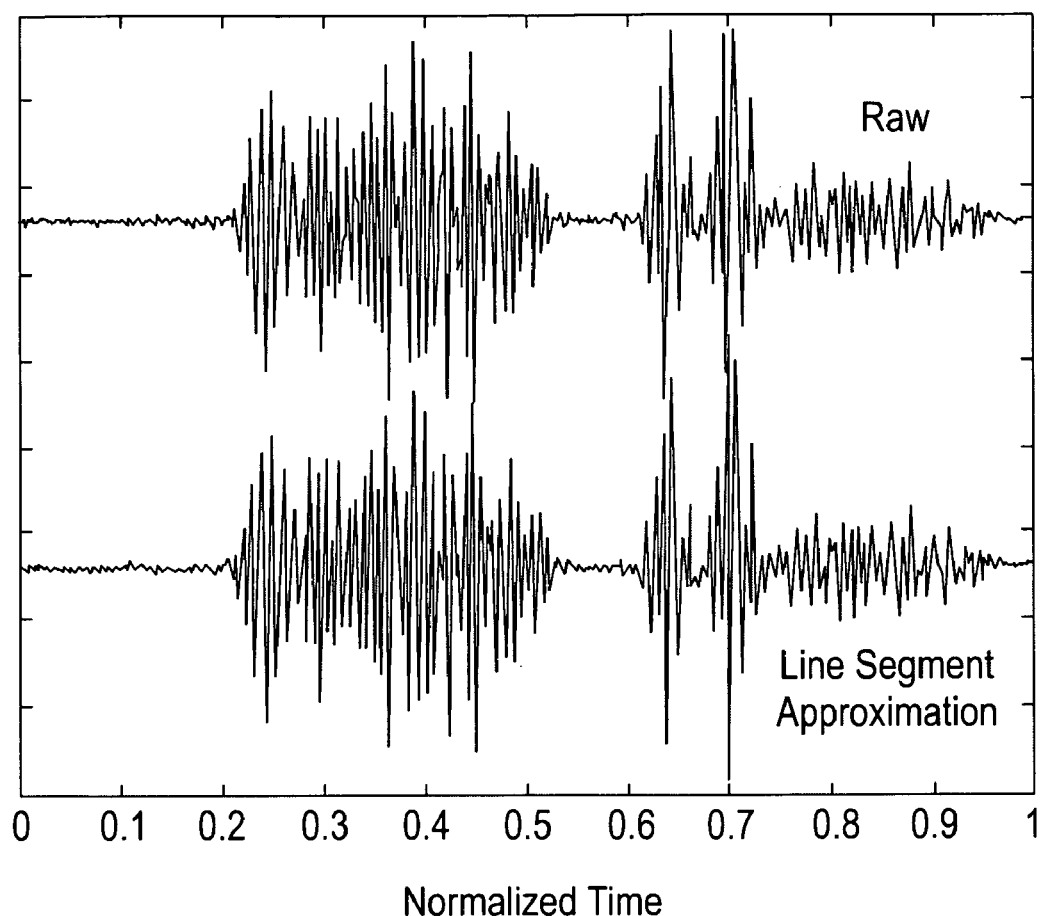
FIG. 3 illustrates a line segment approximation of a recorded sound.
Figure 4A:
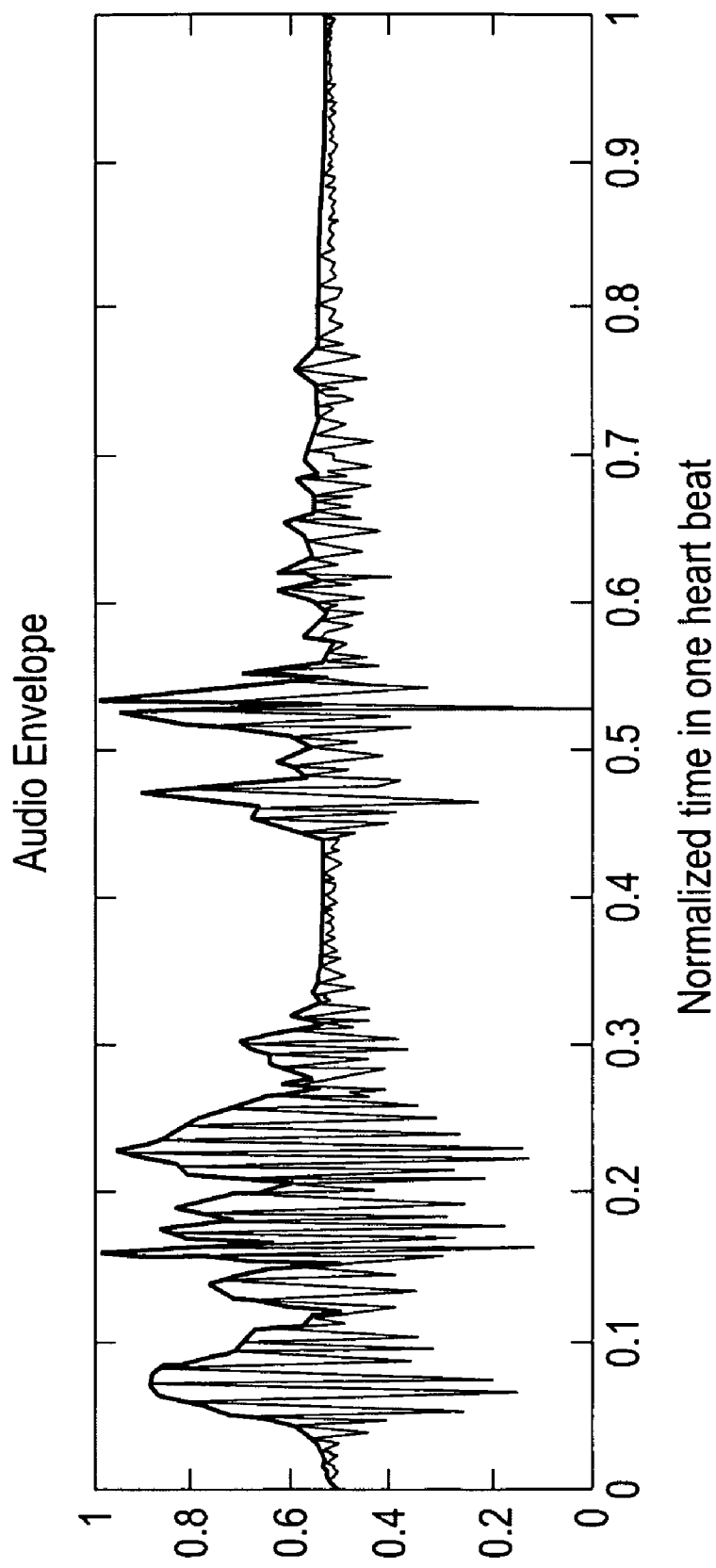
FIG. 4a illustrates an audio envelope matching the line segment approximation of FIG. 3.
Figure 4B:
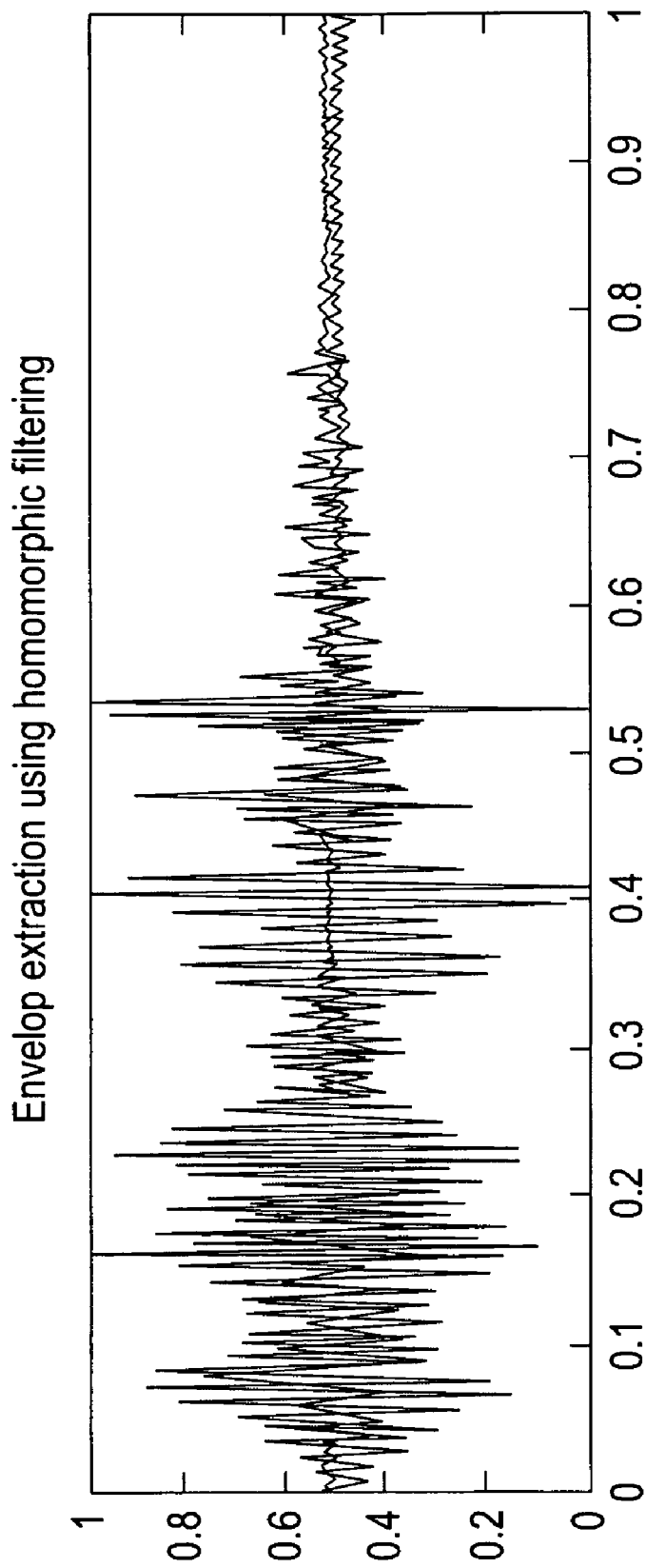
FIG. 4b illustrates a prior art result of using a homomorphic filter on the line segment approximation of FIG. 3.
Figure 5A:
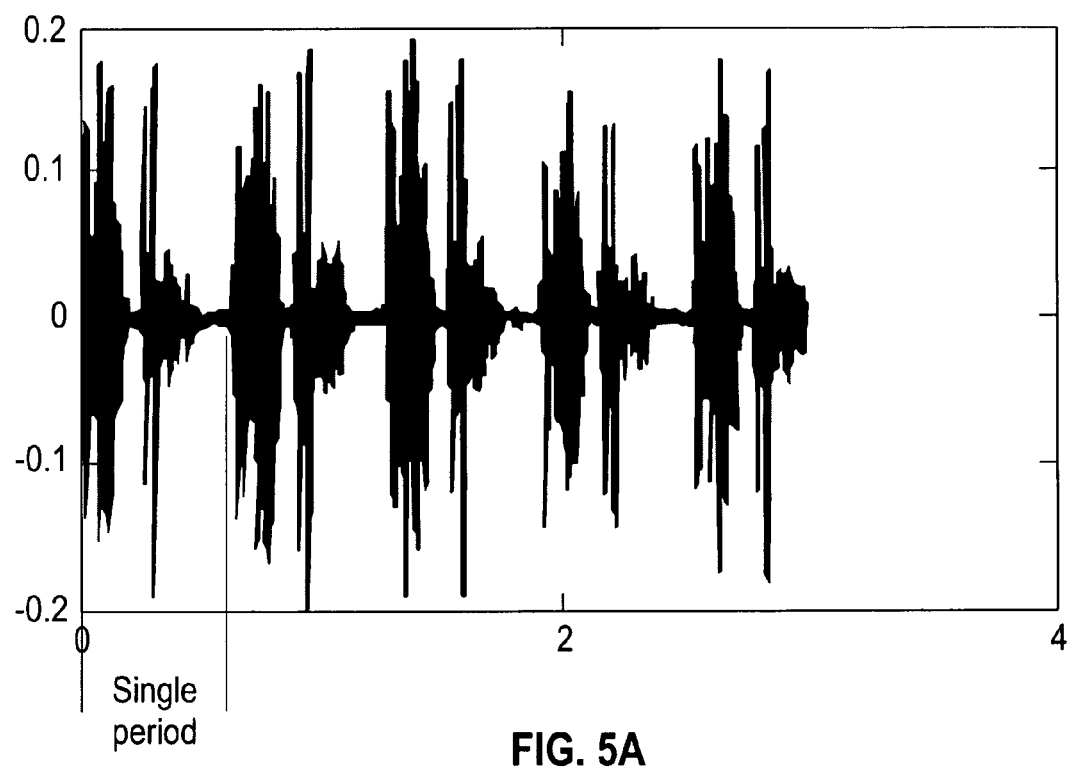
FIGS. 5a and 5b illustrate the results of the pre-processing step of periodicity detection on a recorded heart sound and a database heart sound, respectively.
Figure 5B:
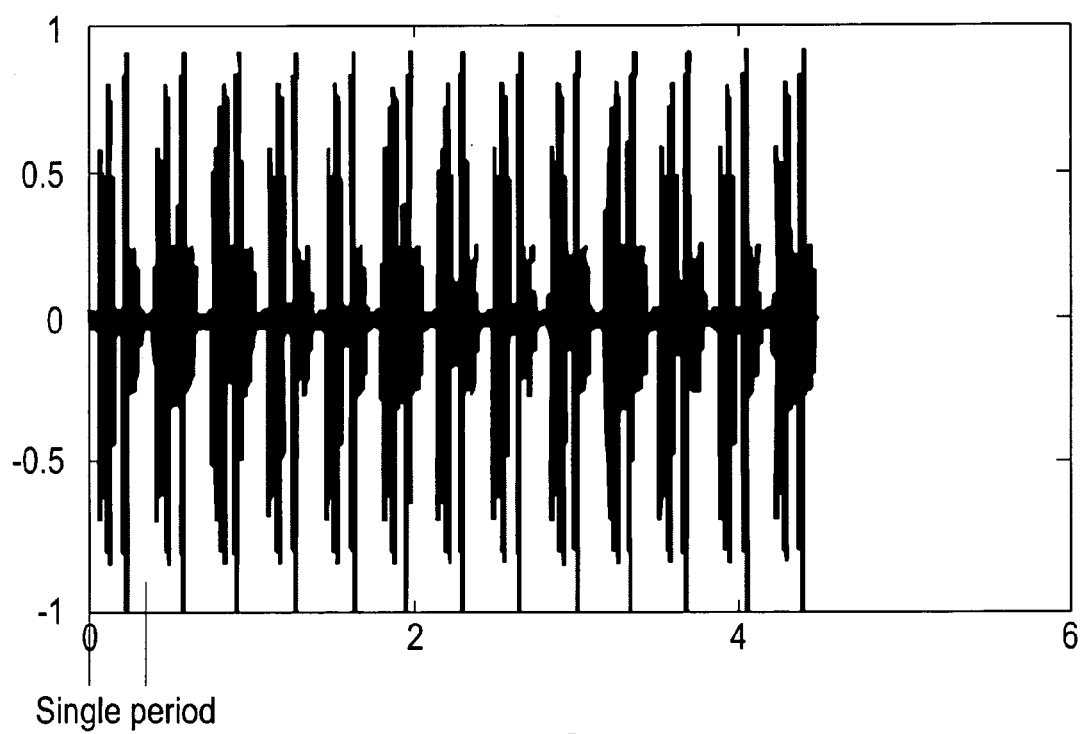
Figure 5C:
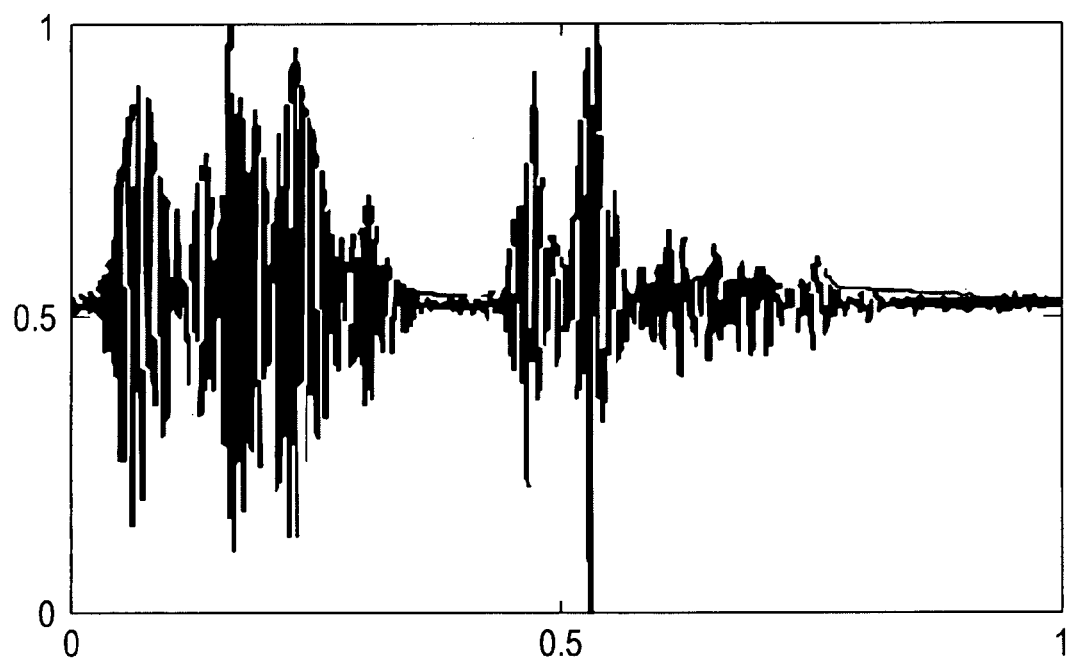
FIGS. 5c and 5d illustrate the results of amplitude and time normalization on a recorded heart sound and a database heart sound, respectively.
Figure 5D:
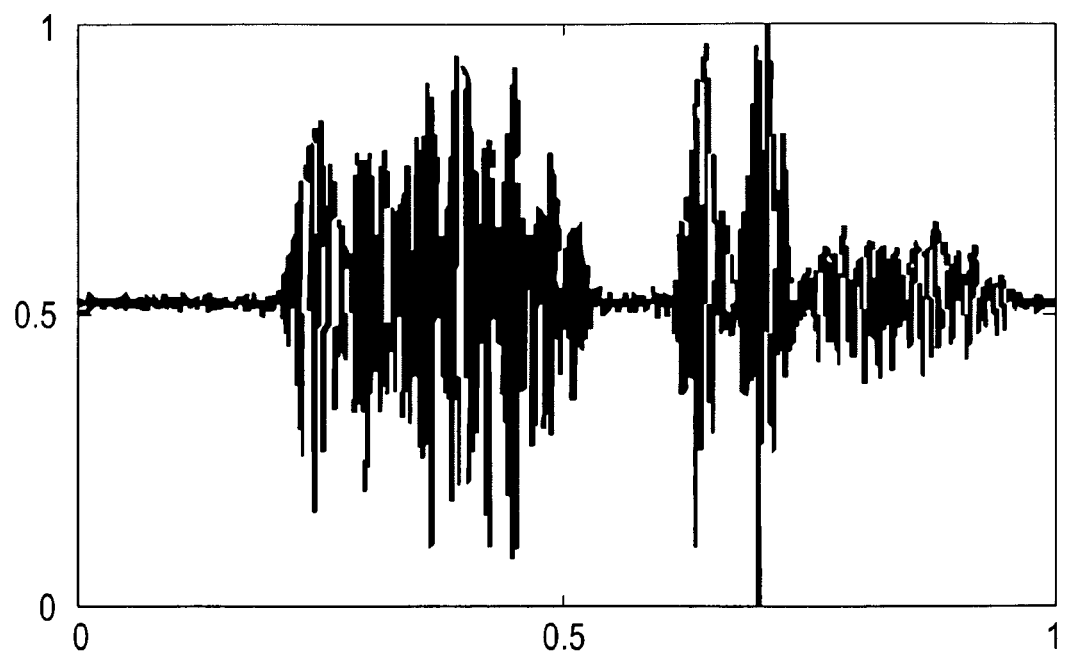
Figure 5E:
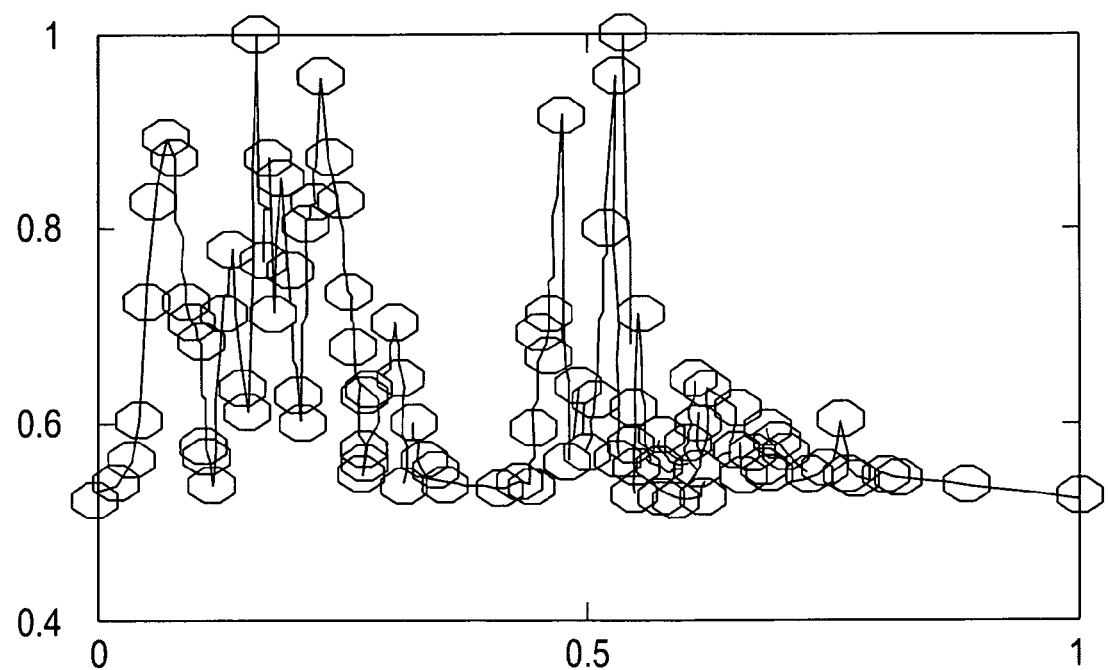
FIGS. 5e and 5f illustrate the fiducial points on the audio envelope of a recorded heart sound and a database heart sound, respectively.
Figure 5F:
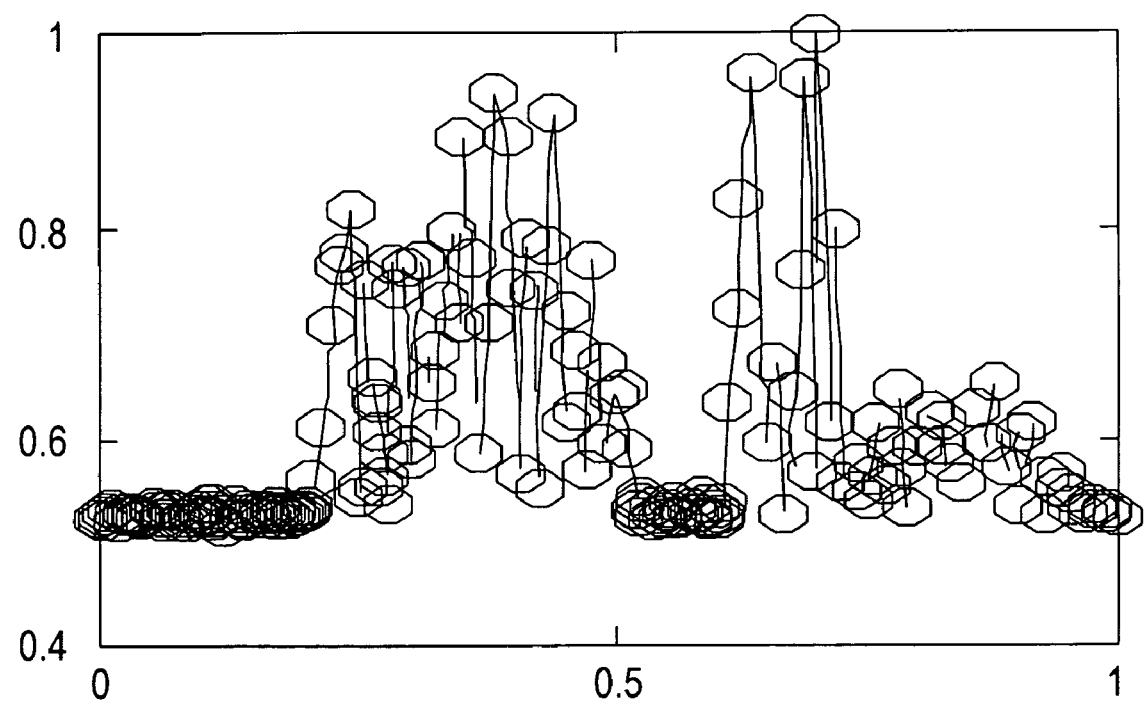
Figure 5G:
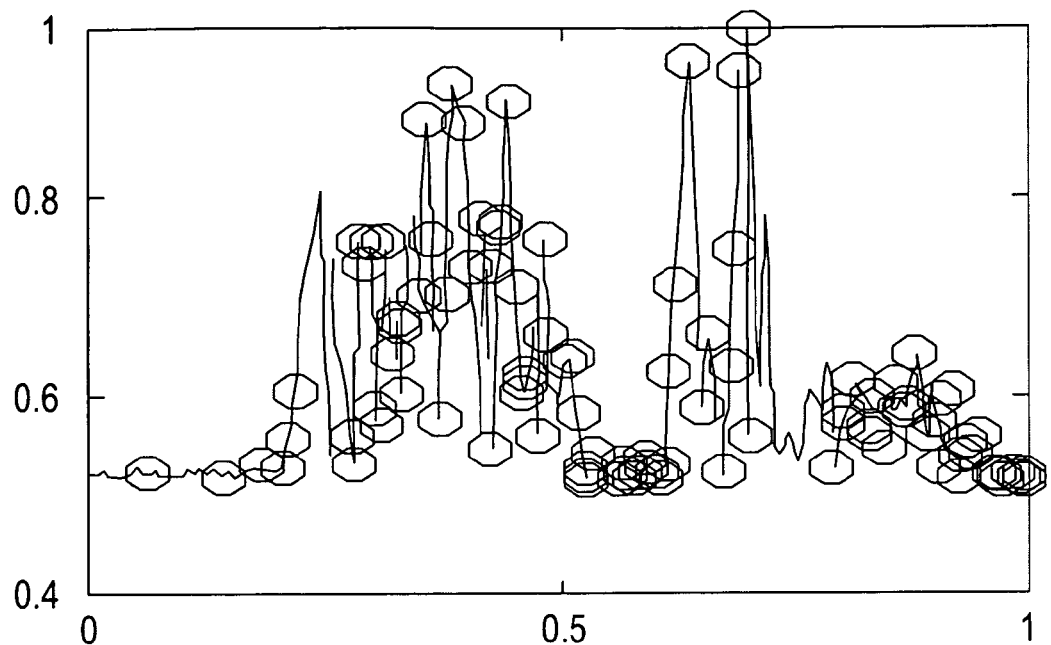
FIG. 5g illustrates the projection of a set of query fiducial points onto the matching database curve.
Figure 5H:
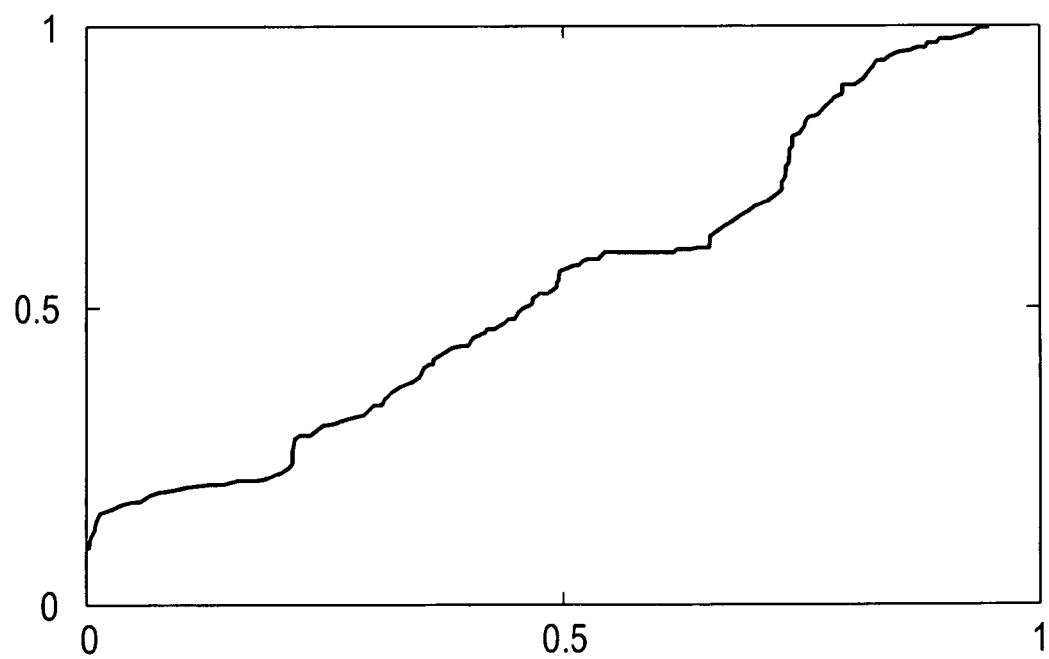
FIG. 5h illustrates the shape-based dynamic time warping alignment used in FIG. 5g.
Figure 6:
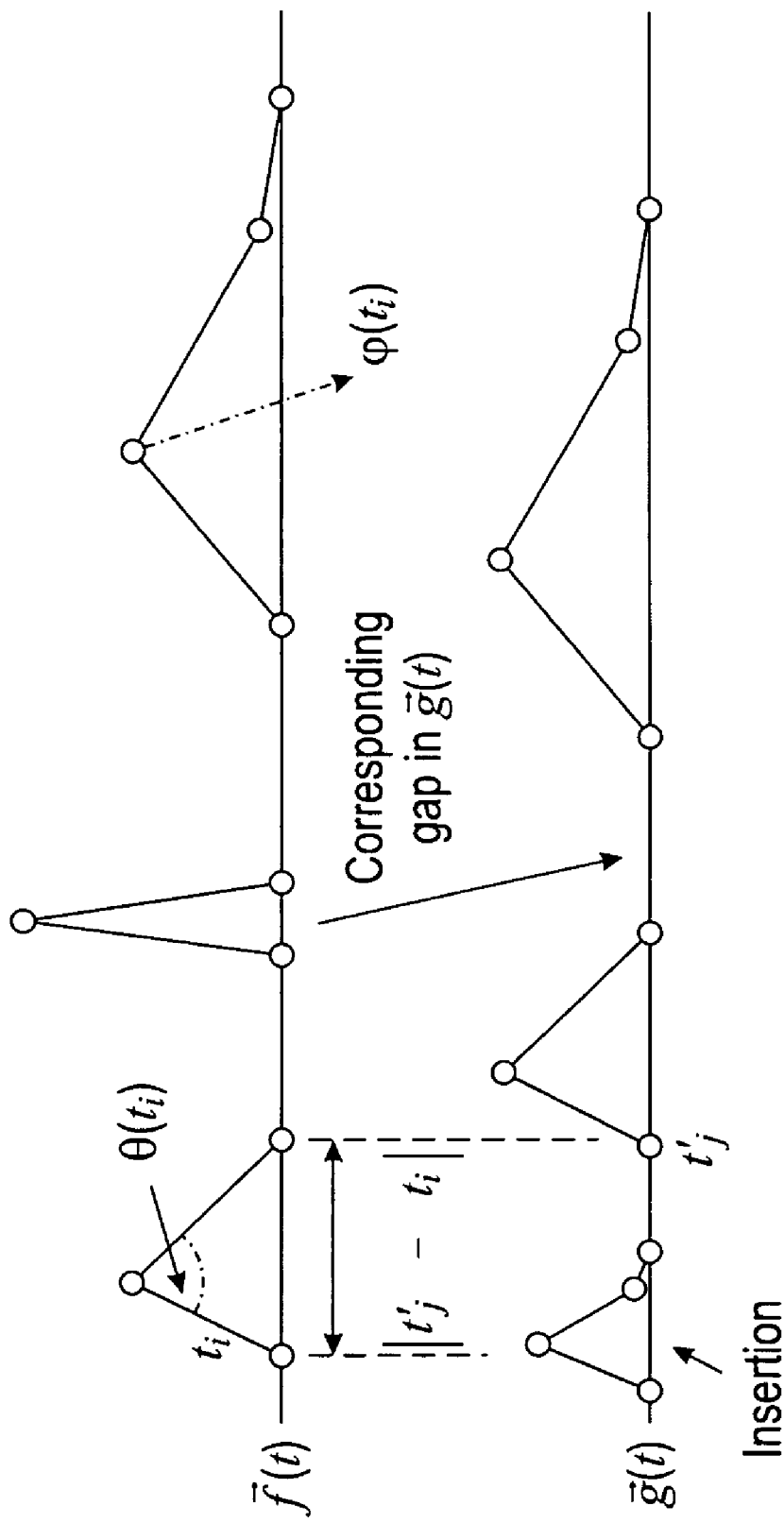
FIG. 6 illustrates the accounting of insertions and gaps in the computation of the match between two sound signals.

FIG. 2 shows the overall operation of the preferred embodiment as performed by computer hardware system 100. Beginning with step 210, microphone 130 records a sound and stores it in memory 120. Processor 110 preprocesses the sound in step 220 by selecting a time period of interest, generally corresponding to one period of a periodic sound, such as a single heart beat. In step 230, processor 110 constructs a line segment approximation of the single period of the sound, as shown in FIG. 4. In step 240, processor 110 defines an audio envelope around the line segment approximation, as shown in FIG. 5. In step 250, processor 110 isolates fiducial points from the audio envelope, as shown in FIG. 6. In step 260, processor 110 matches the fiducial points from audio envelope of the recorded sound with fiducial points from the database sounds obtained through input/output interface 140.

A more detailed discussion of the pre-processing and modeling the shape variation of heart sounds performed by processor 110 will now be presented.

Feature Pre-Processing—Periodicity Detection

While normal heart sounds show good repetition, the periodicity is surprisingly difficult to spot for abnormal heart sounds where the repetitions can be nested or irregular (arrhythmias). Simple auto-correlation is often insufficient for this purpose. A robust periodicity detector treats periodicity detection as the problem of recovering a shift/translation that best aligns two self-similar curves. Consider a periodic curve $g(t)$ with period T. Then by definition $g(t)=g(t+kT)$ for all multiples $k=0, 1, 2, \ldots$. Consider a candidate period $\tau$. Form a curve $f(t)$ by shifting $g(t)$ by $\tau$, i.e.

$$f(t) = \begin{cases} g(t-\tau) & \text{if } t \geq \tau \\ g(t) & \text{otherwise} \end{cases} \quad (1)$$

Then define a function $R(\tau)$ that records the number of curve features that can be verified to satisfy the periodicity condition based on the current estimate of the period as $$R(\tau) = \frac{|\{g(t_i)\}|}{\max\{N-\tau, \tau\}} \text{ such that } |g(t_i) - f(t_j)| \leq \varepsilon \quad (2)$$

where N is the total number of points on the curve, $t_i$ and $t_j$ are time values of matching fiducial points, and $\varepsilon$ is an error tolerance. The above function (2) can be computed in linear time in comparison to the quadratic time for the autocorrelation function. The function $R(\tau)$ shows peaks at precisely those shifts which correspond to periodic repetitions of the curve. The most likely period is then taken as the smallest $\tau$ with the most integer multiples in the allowed range of heart beats (40-180 beats/minute). There may be more than one candidate for period, particularly when the periodic repetitions are nested. The present invention's algorithm finds such overlapping repetitions and tests the dynamic time warping algorithm with each such choice.

Modeling Shape Variations of Audio Envelopes

Various algorithms are available in literature for envelop extraction from signals including homomorphic filtering. While these algorithms are less sensitive to noise-related fluctuations, they frequently extract the low frequency component of the signal rather than render a faithful approximation of the perceptual envelope. In the present invention's approach, the heart sound (within a single heart beat) is modeled through a perceptual envelop.

To extract the audio envelope curve, processor 110 performs noise filtering using wavelet filters to remove the hissing noise that comes from digital stethoscopes. Processor 110 then forms a line segment approximation to the audio signal. This is a standard split-and-merge algorithm for line segment approximation that uses two thresholds, namely, a distance threshold $\delta$ and a line length threshold l to recursively partition the audio signal into a set of line segments. Each consecutive pair of line segments then defines a corner feature $C_i$. With $\delta=0.01$ and $l=5$, a faithful rendering of the audio signal is made possible through a line segment approximation while retaining only 10% of the samples. The thresholds for curve parameterization are not as critical here as the shape matching algorithm presented below, which is robust to missing and spurious features. The audio envelope (AE) is defined as the set of points $AE=\{P_i\}$ where $P_i=C_j$ for some j such that $$P_i(y) \geq P_{i-1}(y) \& P_i(y) \geq P_{i+1}(y) \text{ and } P_i(y) \geq \text{baseline}. \quad (1)$$

Only the values of the signal above the baseline are retained in the maxima envelope curve. Similarly, all peaks below the baseline for the minima envelope curve.

Once the envelope curve $f(t)$ is extracted, its shape can be represented by the curvature change points or corners on the envelope curve. The shape information at each corner is captured using the following parameters, wherein these parameters are chosen to facilitate matching of audio envelopes:

$$S(\vec{f}(t_i)) = <t_i, \vec{f}(t_i), \theta(t_i), \phi(t_i)> \quad (2)$$

where $\theta(t_i)$ is the included angle in the corner at $t_i$, and $\phi(t_i)$ is the orientation of the bisector at corner $t_i$. Using the angle of the corner ensures that wider complexes are not matched to narrow complex as these can change the disease interpretation. The angular bisector, on the other hand, ensures that polarity reversals such as inverted waves can be captured.

Modeling Morphological Shape Variations

Referring to FIG. 6, consider an envelope curve g(t) corresponding to a heart sound. Consider another curve f(t) that is a potential match to g(t), i.e. comes from a different patient diagnosed with the same disease. The curve f(t) is considered perceptually similar to g(t) if a non-rigid transform characterized by [a,b,Γ] can be found such that $$|f'(t)-g(t)| \leq \delta \quad (3)$$

where | | represents the distance metric that measures the difference between f'(t) and g(t), the simplest being the Euclidean norm and $$f(t)=af(\Phi)(t)) \text{ with } \Phi(t)=bt+\gamma(t) \quad (4)$$

where the (bt) is the linear component of the transform and Γ is the non-linear translation component. The parameters a and b are recovered by normalizing in amplitude and time. Normalizing in amplitude is done by transforming f(t) and g(t) such that $$\hat{f}(t) = \frac{f(t) - f_{min}(t)}{f_{max}(t) - f_{minf}(t)} \text{ and} \quad (5)$$

$$\hat{g}(t) = \frac{g(t) - g_{min}(t)}{g_{max}(t) - g_{minf}(t)}$$

so that a=1. To eliminate solving for b, normalization of the time axis is done by dividing the heart rate. Suppose the sampling rate of points on the curve f(t) is FS. Let a periodicity detection algorithm signal the heart rate period to be $T_1$. Dividing by the heart period samples, all time instants lie in the range [0,1]. Thus the time normalization can be easily achieved as:

$$\vec{f}(t)=\hat{f}(t/T_1); \vec{g}(t)=\hat{g}(t/T_2) \quad (6)$$

where $T_1$ and $T_2$ are the heart beat durations of f(t) and g(t) respectively. With this time normalization, b=1. Such amplitude and time normalization automatically makes the shape modeling invariant to amplitude variations in audio recordings, as well as variations in heart rate across patients. Since the non-uniform translation Γ is a function of t, computational overhead is avoided by recovering it at important fiducial points such as the corners, and the overall shape approximation is recovered by interpolation. Let there be K features extracted from $\vec{f}(t)$ as $F_K = \{(t_1, \vec{f}_1(t_1)), (t_2, \vec{f}_2(t_2)), \ldots (t_K, \vec{f}_K(t_K))\}$ at time $\{t_1, t_2, \ldots, t_K\}$ respectively. Let there be M fiducial points extracted from $\vec{g}(t)$ as $G_M = \{(t'_1, \vec{g}_1(t'_1)), (t'_2, \vec{g}_2(t'_2)), \ldots (t'_M, \vec{g}_M(t'_M))\}$ at time $\{t'_1, t'_2, \ldots t'_M\}$, respectively. If there is a set of N matching fiducial points $C_\Gamma = \{(t_i, t'_j)\}$, then the non-uniform translation transform Γ can be defined as:

$$\Gamma(t) = \begin{cases} t_i & \text{if } t = t'_j \text{ and } t_i, t'_j \in C_\Gamma \\ t_r + \left(\frac{t_s - t_r}{t'_l - t'_k}\right)(t - t'_k) & \text{where } (t_r, t'_k), (t_s, t'_l) \in C_\Gamma \end{cases} \quad (7)$$

and $t'_k$ is the highest of $t'_j \leq t$ and $t'_l$ is the lowest of $t'_j \geq t$ that have a valid mapping in $C_\Gamma$. Other interpolation methods besides linear (e.g., spline) are also possible.

Using Equations 6 and 7, the shape approximation error between the two curves is then given by:

$$|f'(t)-g(t)|=|\vec{f}(\Gamma(t))-\vec{g}(t)| \quad (8)$$

For each g(t), Γ is selected such that it minimizes the approximation error in (6) while maximizing the size of match $C_\Gamma$. Finding the best matching audio based on shape can then be formulated as finding the g(t) such that $$g_{best} = \arg\min_g |\vec{f}(\Gamma(t)) - \vec{g}(t)| \quad (9)$$

while choosing the best Γ for each respective candidate match g(t).

If the feature set $F_K$, $G_M$ extracted from the respective curves is considered as sequences, the problem of computing the best Γ reduces to finding the best global subsequence alignment using the dynamic programming principle. The best global alignment maximizes the match of the curve fragments while allowing for possible gaps and insertions. Gaps and insertions correspond to signal fragments from feature set $F_K$ that don't find a match in set $G_M$ and vice versa. In fact, the alignment can be computed using a dynamic programming matrix H where the element H(i,j) is the cost of matching up to the ith and jth element in the respective sequences. As more features find a match, the cost increases as little as possible. The dynamic programming step becomes:

$$H_{i,j} = \min \begin{cases} H_{i-1,j-1} + d(\vec{f}(t_i), \vec{g}(t'_j)) \\ H_{i-1,j} + d(\vec{f}(t_i), 0) \\ H_{i,j-1} + d(0, \vec{g}(t'_j)) \end{cases} \quad (10)$$

with initialization as $H_{o,o}=0$ and $H_{o,j}=\infty$ and $H_{i,0}=\infty$ for all $0<i \leq K$, and $0<j \leq M$. Here d(.) is the cost of matching the individual features described next. Also, the first term represents the cost of matching the feature point $\vec{f}(t_i)$ to feature point $\vec{g}(t'_j)$ which is low if the features are similar. The second term represents the choice where no match is assigned to feature $\vec{f}(t_i)$.

Shape Similarity of Envelop Curves

After the transformation is recovered, the similarity between two envelop curves is given by the cost function d($\vec{f}(t_i), \vec{g}(t'_j)$):

$$d(\vec{f}(t_i), \vec{g}(t'_j)) = \begin{cases} \sqrt{(t_i - t'_j)^2 + (\vec{f}(t_i) - \vec{g}(t'_j))^2 + (\theta(t_i) - \theta(t'_j))^2 + (\varphi(t_i) - \varphi(t'_j))^2} & \text{if } |t_i - t'_j| \leq \text{ and } (\vec{f}(t_i) - \vec{g}(t'_j))^2 \leq \lambda_2 |\theta(t_i) - \theta(t'_j)| \leq \lambda_3 |\varphi(t_i) - \varphi(t'_j)| \leq \lambda_4 \\ \infty & \text{otherwise} \end{cases} \quad (11)$$

The thresholds ($\lambda_1, \lambda_2, \lambda_3, \lambda_4$) are determined through a prior learning phase in which the expected variations per disease class is noted. The cost function $d(\vec{f}(t_i),0)$ can be computed by substituting $t'_j=0$, $\vec{g}(t'_j)=0$ and $\theta(t+_j)=0$, $\phi(t'_j)=0$ in Equation 11. The cost function $d(0,\vec{g}(t'_j))$ can be similarly computed.

Thus using the present invention's approach, two heart sounds are considered similar if enough number of fiducial points between query and target envelop curves can be matched using shape-based dynamic time warping. In general, due to the period estimation offset errors, the signals may have to be circularly shifted by a fixed translation for a rough alignment before the fine non-rigid alignment described above.

Additionally, the present invention provides for an article of manufacture comprising computer readable program code contained within implementing one or more modules to detect audio similarity of sounds. Furthermore, the present invention includes a computer program code-based product, which is a storage medium having program code stored therein which can be used to instruct a computer to perform any of the methods associated with the present invention. The computer storage medium includes any of, but is not limited to, the following: CD-ROM, DVD, magnetic tape, optical disc, hard drive, floppy disk, ferroelectric memory, flash memory, ferromagnetic memory, optical storage, charge coupled devices, magnetic or optical cards, smart cards, EEPROM, EPROM, RAM, ROM, DRAM, SRAM, SDRAM, or any other appropriate static or dynamic memory or data storage devices.

Implemented in computer program code based products are software modules for recording a sound, selecting a time duration of a portion of the first sound to use as a second sound, constructing a line segment approximation of the second sound, defining an audio envelope around the second sound using the line segment approximation, isolating a plurality of fiducial points on the audio envelope, and matching the second sound to a plurality of similar sounds, wherein the matching comprises: identifying a non-rigid alignment transform based on a shape-based dynamic time warping to determine a correspondence between the fiducial points of the audio envelope and fiducial points from a database of sounds, defining a measure of shape similarity by determining a ratio of matched fiducial points to a total number of fiducial points, and ranking the matching based on the ratio.

CONCLUSION

A system and method has been shown in the above embodiments for the effective implementation of a method and apparatus for retrieval of sounds from a database. While various preferred embodiments have been shown and described, it will be understood that there is no intent to limit the invention by such disclosure, but rather, it is intended to cover all modifications falling within the spirit and scope of the invention, as defined in the appended claims. For example, the present invention should not be limited by the type of audio.

The above enhancements are implemented in various computing environments. For example, the present invention may be implemented on a conventional IBM PC or equivalent, multi-nodal system (e.g., LAN) or networking system (e.g., Internet, WWW, wireless web). All programming and data related thereto are stored in computer memory, static or dynamic, and may be retrieved by the user in any of: conventional computer storage, display (i.e., CRT) and/or hardcopy (i.e., printed) formats. The programming of the present invention may be implemented by one of skill in the art of audio analysis.

The invention claimed is:

1. A computer-implemented method for detecting audio similarity of heart sounds, said computer-implemented method implemented by executing computer readable program code in a processor, said method comprising:
    recording a first heart sound;
    pre-processing the first heart sound to create a second heart sound;
    constructing a line segment approximation of the second heart sound;
    defining an audio envelope around the second heart sound using the line segment approximation, said audio envelope having a plurality of fiduciary points;
    isolating said plurality of fiducial points on the audio envelope;
    matching the second heart sound to a plurality of similar stored heart sound in a database based on said isolated fiducial points and fiducial points associated with said stored heart sounds in said database, said matching based on a function of matched fiducial points and a total number of fiducial points; and
    outputting the matched similar heart sounds.

2. The method of claim 1, wherein the step of pre-processing comprises identifying a single periodic segment.

3. The method of claim 1, wherein the matching comprises:
    identifying a non-rigid alignment transform based on a shape-based dynamic time warping to determine a correspondence between the fiducial points of said audio envelope and fiducial points from said database of heart sounds;
    defining a measure of shape similarity as said function of a number matched fiducial points and a total number of fiducial points; and
    outputting the measure of shape similarity.

4. The method of claim 3, wherein the function comprises a ratio of the number of matched fiducial points to the total number of fiducial points.

5. The method of claim 4, wherein the matching further comprises ranking the matching based on the ratio.

6. The method of claim 3, wherein the database of heart sounds comprises a database of heart sounds associated with diseases.

7. The method of claim 6, wherein the step of outputting the measure of shape similarity further comprises:
    assembling disease statistics from the database of heart sounds; and
    presenting the disease statistics as a decision support system showing disease labels that are associated with a plurality of heart sounds from the database of heart sounds.

8. The method of claim 3, wherein the matching further comprises time scaling and amplitude scaling.

9. The method of claim 1, wherein the fiducial points comprise local extremes of the audio envelope only on one side of a baseline of the second heart sound.

10. A computer program product comprising:
    a non-transitory computer storage medium having computer usable program code for detecting audio similarity of heart sounds, said computer program product including:
    computer usable program code for recording a first heart sound;

computer usable program code for pre-processing the first heart sound, wherein the computer usable program code for pre-processing comprises:
- program code for selecting a time duration of a portion of the first heart sound to use as a second heart sound;
- computer usable program code for constructing a line segment approximation of the second heart sound;
- computer usable program code for defining an audio envelope around the second heart sound using the line segment approximation, said audio envelope having a plurality of fiduciary points;

computer usable program code for isolating said plurality of fiducial points on the audio envelope; and
- computer usable program code for matching the second heart sound to a plurality of similar heart sounds, wherein the computer usable program code matching comprises:
- program code for identifying a non-rigid alignment transform based on a shape-based dynamic time warping to determine a correspondence between the fiducial points of the audio envelope and fiducial points from a database of heart sounds;
- program code for defining a measure of shape similarity by determining a ratio of matched fiducial points to a total number of fiducial points;
- program code for ranking the matching based on the ratio; and
- computer usable program code for outputting ranked matches.

11. A system for detecting audio similarity of heart sounds comprising: an audio transducer for recording a first heart sound; a processor; wherein the processor is configured to pre-processes the first heart sound to create a second heart sound, constructs a line segment approximation of the second heart sound, defines an audio envelope around the second heart sound using the line segment approximation, and isolates a plurality of fiducial points on the audio envelope; an input/output interface is configured to communicate with a database of heart sounds; wherein the processor matches the second heart sound to a plurality of similar heart sounds retrieved from the database through the input-output interface, said matching comprising: identifying a non-rigid alignment transform based on a shape-based dynamic time warping to determine a correspondence between the fiducial points of the audio envelope and fiducial points from a database of heart sounds; defining a measure of shape similarity as a function of a number matched fiducial points and a total number of fiducial points; and outputting the measure of shape similarity.

12. The system of claim 11, wherein the function comprises a ratio of the number of matched fiducial points to the total number of fiducial points.

13. The system of claim 12, wherein the processor ranks the matching based on the ratio.

14. The system of claim 11, wherein the database of heart sounds comprises a database of heart sounds associated with diseases.

15. The system of claim 14, wherein outputting the measure of shape similarity further comprises:
- assembling disease statistics from the database of heart sounds; and
- presenting the disease statistics as a decision support system showing disease labels that are associated with a plurality of heart sounds from the database of heart sounds.

16. The system of claim 11, wherein the processor is configured to adjust the second heart sound by time scaling and amplitude scaling.

17. The system of claim 11, wherein the fiducial points comprise local extremes of the audio envelope only on one side of a baseline of the second heart sound.

* * * * *